(12) United States Patent
Stock

(10) Patent No.: US 6,923,040 B2
(45) Date of Patent: Aug. 2, 2005

(54) DEVICE AND PROCESS FOR MEASURING BREATH ALCOHOL

(75) Inventor: Burkhard Stock, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 34 days.

(21) Appl. No.: 10/721,677

(22) Filed: Nov. 25, 2003

(65) Prior Publication Data

US 2004/0154377 A1 Aug. 12, 2004

(30) Foreign Application Priority Data

Feb. 11, 2003 (DE) .......................................... 103 05 392

(51) Int. Cl.$^7$ ............................................... G01N 1/22
(52) U.S. Cl. ...................................................... 73/23.3
(58) Field of Search ............................. 73/23.2, 23.21, 73/23.3; 702/24

(56) References Cited

U.S. PATENT DOCUMENTS

| | | | |
|---|---|---|---|
| 4,297,871 A | * 11/1981 | Wright et al. ................. | 73/23.3 |
| 5,048,321 A | * 9/1991 | Chow ........................... | 73/23.3 |
| 5,369,977 A | * 12/1994 | Rhodes et al. ............... | 73/23.3 |
| 5,612,896 A | * 3/1997 | Stock ........................... | 702/24 |
| 5,739,412 A | 4/1998 | Stock et al. | |
| 6,167,746 B1 | 1/2001 | Gammenthaler | |
| 6,289,718 B1 | * 9/2001 | Stock ........................... | 73/23.2 |

FOREIGN PATENT DOCUMENTS

| | | | | |
|---|---|---|---|---|
| DE | 44 43 142 | | 6/1996 | |
| GB | 2295679 A | * | 6/1996 | ......... G01N/33/497 |

\* cited by examiner

*Primary Examiner*—Charles Garber
(74) *Attorney, Agent, or Firm*—McGlew and Tuttle, P.C.

(57) ABSTRACT

A device for measuring breath alcohol has a mouthpiece (1) for picking up the exhaled respiratory gas volume flow of a person to be measured. The mouthpiece has a flow diaphragm (3). A pressure sensor (4) is connected via a first gas line to the mouthpiece (1) upstream of the flow diaphragm (3). A breath alcohol sensor (10) is connected via a inlet channel (6) to the mouthpiece (1) downstream of the flow diaphragm (3) and via a second gas line (11) to a sampling system (7, 8, 9) for a respiratory gas sample from the respiratory gas volume flow. An evaluation and control unit (5) receives the measured signals of the pressure sensor (4) and of the breath alcohol sensor (10) and actuates the sampling system (7, 8, 9). The sampling system (7, 8, 9) is designed such that two respiratory gas samples are fed, in a time sequence, into the breath alcohol sensor (10), whereby the volume of the first respiratory gas sample is at most 40% of the volume of the second one.

6 Claims, 1 Drawing Sheet

US 6,923,040 B2

DEVICE AND PROCESS FOR MEASURING BREATH ALCOHOL

FIELD OF THE INVENTION

The present invention pertains to a device for measuring breath alcohol and to a process for measuring breath alcohol.

BACKGROUND OF THE INVENTION

Breath alcohol measurements are known per se and are carried out with different measuring devices and processes. E.g., a measuring device emerges from U.S. Pat. No. 6,167, 746 B1 that comprises a graduated tube, to which are connected a pressure sensor and a temperature sensor one after the other, viewed in the direction of gas flow, as well as a gas sampling valve with an electrochemical measuring cell downstream of this valve for the measurement of the breath alcohol concentration.

Prior-art breath alcohol measuring devices, e.g., the Alcotest® devices, have been used for several years for the specific monitoring of the breath alcohol concentration of drivers, especially in traffic checks.

It is well known that breath alcohol measurements can be considerably distorted by the detection of mouth alcohol, since, when mouth alcohol is present, the measured breath alcohol concentration is markedly higher at the beginning of a breathing-out process than at the end. Contrary to this, in the case of a normal respiratory gas sample without mouth alcohol detecting only deep pulmonary gas, the measured breath alcohol concentration increases as a function of exhaled respiratory gas volume or as a function of duration of exhalation. Therefore, a process for detecting the presence of mouth alcohol in a respiratory gas sample has been suggested according to DE 44 43 142 C2, whereby a first respiratory gas sample at the beginning of an exhalation stroke is fed into a measuring cell of a breath alcohol measuring device and a first measurement curve is recorded, and at a second point in time during the same exhalation stroke, if mouth alcohol affects the measurement markedly less, a second respiratory gas sample is fed into the measuring cell of the breath alcohol measuring device and a second measurement curve is recorded. Characteristic parameters, and especially the integral values or maximum values of measurement curves are obtained from each of the two measurement curves and compared to one another, so that, e.g., based on the ratio of the maximum values, it can be determined whether mouth alcohol distorts the measurement, so as to discard the measurement result in this case.

This prior-art process has the drawback that very fast sensors would have to be used for measuring the concentration; thus, depending on the respiratory gas sampling, the measured signal for the first respiratory gas sample has already subsided when the second respiratory gas sample is measured, so that there is practically no longer an overlapping of the two mouth alcohol/respiratory gas alcohol measured effects. Typical practical values for the measurement times are about one second after the beginning of exhalation for the first respiratory gas sampling and about five seconds for the second respiratory gas sampling.

It has now been shown that an exact mathematical separation of the two measured signals cannot be achieved, such that the end-expiratory breath alcohol measurement continues to have errors. These errors are essentially caused by the property of the electrochemical sensors desired in measurement practice that especially measuring sensitivity and reaction speed decrease if these sensors are gassed shortly one after the other. The measurement errors are greater, the higher the alcohol concentration is, e.g., gassing with an alcohol concentration of 1% requires a waiting time of one minute, in order to keep this fatigue effect of the electrochemical sensors negligibly small.

SUMMARY OF THE INVENTION

Consequently, the object of the present invention is to provide a device and a process for measuring breath alcohol with an improved measured signal quality, so that two breath alcohol measurements can be carried out within the maximum time window of a few seconds after the beginning of the exhalation process, which is relevant for practice, and it can be determined whether mouth alcohol distorts the measurement.

According to the invention, a device for measuring breath alcohol is provided with a mouthpiece for picking up the exhaled respiratory gas volume flow of a person to be measured. The mouthpiece has a flow diaphragm. A pressure sensor is connected via a first gas line to the mouthpiece upstream of the flow diaphragm. A breath alcohol sensor is connected via an inlet channel to the mouthpiece downstream of the flow diaphragm and via a second gas line to a sampling system for a respiratory gas sample from the respiratory gas volume flow. An evaluation and control unit receives the measured signals of the pressure sensor and of the breath alcohol sensor and actuates the sampling system. The sampling system is designed such that two respiratory gas samples are fed, in a time sequence, into the breath alcohol sensor, whereby the volume of the first respiratory gas sample is at most 40% of the volume of the second one.

According to another aspect of the invention, a process is provided for measuring breath alcohol with a mouthpiece for picking up the exhaled respiratory gas volume flow of a person to be measured, whereby the mouthpiece is provided with a flow diaphragm. A pressure sensor is connected via a first gas line to the mouthpiece upstream of the flow diaphragm. A breath alcohol sensor is connected via an inlet channel to the mouthpiece downstream of the flow diaphragm and via a second gas line to a sampling system for a respiratory gas sample from the respiratory gas volume flow. An evaluation and control unit receives the measured signals of the pressure sensor and the breath alcohol sensor and actuates the sampling system. The discharged respiratory gas volume is determined by the evaluation and control unit based on the pressure of the respiratory gas volume flow measured at the diaphragm and by time integration. The sampling system is actuated by the evaluation and control unit for a respiratory gas sampling in the breath alcohol sensor at two different time points after the beginning of the respiratory gas volume flow detected by means of the pressure sensor. The volume of the first respiratory gas sample is at most 40% of the volume of the second respiratory gas sample. The second respiratory gas sample is taken only if a certain, predetermined respiratory gas volume is reached within a certain, predetermined time.

A fundamental advantage of the device and process according to the present invention is that, due to the double respiratory gas sampling, on the one hand, it can be determined with good certainty whether mouth alcohol is present in the respiratory gas sample, and, on the other hand, it is possible to exactly analyze measured signals of the breath alcohol content correlating with the blood alcohol concentration.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The sole FIGURE is a schematic view showing a device according to the present invention.

DESCRIPTION OF THE PREFERRED EMBODIMENT

Figure 1:
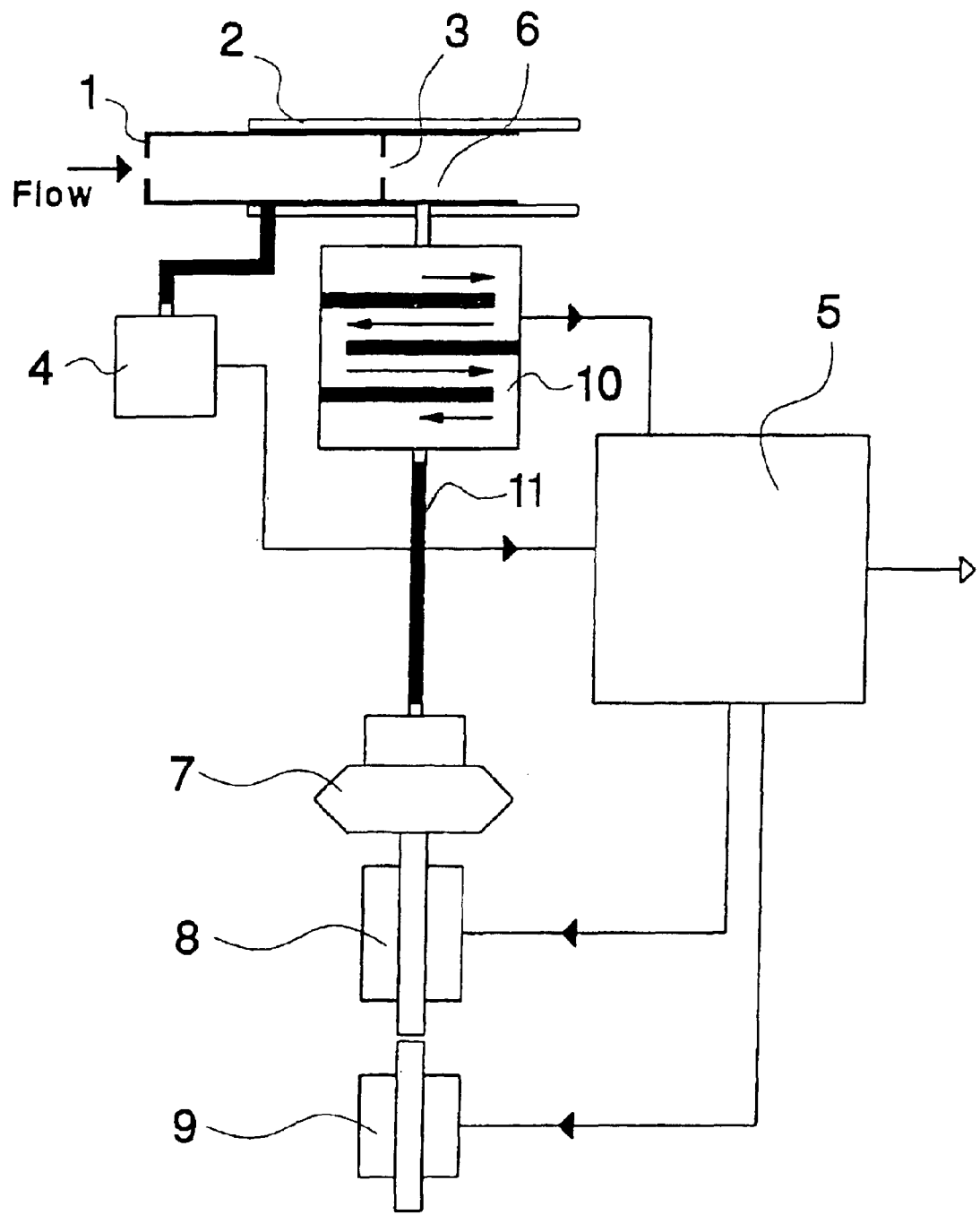

Referring to the drawings in particular, a preferably replaceable mouthpiece 1, into which the person to be measured blows, whose breath alcohol concentration is measured, is inserted into a recorder 2. At the flow diaphragm 3, which has a circular flow cross section with a diameter of about 3 to 4 mm, the "flow" (respiratory gas volume flow) produces a dependent pressure drop in accordance with natural laws for this. The pressure in front of the flow diaphragm 3 is measured with a pressure sensor 4, whose measurement junction is connected via a first gas line to the mouthpiece 1 in the recorder 2 upstream of the flow diaphragm 3. The evaluation and control unit 5 receives the measured pressure signal from the pressure sensor 4 and calculates the respiratory gas volume flow as well as the respiratory gas volume discharged from this due to integration. Behind, i.e., downstream of, the flow diaphragm 3 is located the inlet channel 6 of the breath alcohol sensor 10. Through the inlet channel 6 a respiratory gas sample is drawn from the respiratory gas flow into the breath alcohol sensor 10 at different times via the second gas line 11 by means of a sampling system 7, 8, 9. The sampling system 7, 8 and 9 comprises the elastic bellows 7 and two lifting magnets 8 and 9. As the person, whose breath alcohol concentration is to be measured, has discharged a certain minimum respiratory gas volume. At the start of the first sampling, a current pulse is sent by the evaluation and control unit 5 to the first lifting magnet 8, e.g., 1 second after the beginning of exhaling, as a result of which the lifting magnet 8 partly compresses the bellows 7. After switching off the current, the bellows 7 expands again and suctions a structurally defined first respiratory gas volume through the breath alcohol sensor 10, where the alcohol is quickly absorbed by the surface of the electrochemical gas sensor that is preferably used and due to a characteristic electrochemical detection reaction leads to a concentration-dependent measured signal for the breath alcohol content of the person measured and can then be further evaluated in the known manner. The second lifting magnet 9 is actuated by the evaluation and control unit 5 at a second time point during the process of exhaling, e.g., 5 seconds after the beginning of the exhalation process, so that the bellows 7 this time is compressed more greatly than for the first sampling. Thus, a second respiratory gas volume is fed through the breath alcohol sensor 10 for measurement. The lifting magnets 8, 9 are designed, such that the first respiratory gas volume is only about 30% to 40% of the second one.

To now determine the breath alcohol concentration at the beginning and at the end of the exhalation process, the individual signals from both pump operations are calculated from the time-dependent, compound, measured signal. The maxima of the separated signals are subsequently compared. The mouth alcohol is present if the maximum of the measurement curve that is measured first in time is markedly greater, e.g., at least 10%, than the maximum of the measurement curve that is measured secondly in time corresponding to the end-expiratory breath alcohol concentration.

While a specific embodiment of the invention has been shown and described in detail to illustrate the application of the principles of the invention, it will be understood that the invention may be embodied otherwise without departing from such principles.

What is claimed is:

1. A device for measuring breath alcohol, the device comprising:

a mouthpiece for picking up the exhaled respiratory gas volume flow of a person to be measured;

a flow diaphragm provided in said mouthpiece;

a pressure sensor connected via a first gas line to the mouthpiece upstream of the flow diaphragm;

a breath alcohol sensor;

an inlet channel connecting said breath alcohol sensor to said mouthpiece downstream of the flow diaphragm;

a sampling system for sampling the respiratory gas sample from the respiratory gas volume flow;

a second gas line connecting said breath alcohol sensor to said sampling system;

an evaluation and control unit receiving measured signals of said pressure sensor and of said breath alcohol sensor and actuating said sampling system, said sampling system feeding two respiratory gas samples, in a time sequence, into said breath alcohol sensor, whereby a volume of a first respiratory gas sample is at most 40% of the volume of a second respiratory gas sample.

2. A device in accordance with claim 1, wherein said sampling system has two lifting magnets acting on a bellows such that a first lifting magnet has a stroke that is 30% to 40% of a stroke of said second lifting magnet.

3. A process for measuring breath alcohol comprising the steps of:

providing a mouthpiece having a flow diaphragm;

picking up an exhaled respiratory gas volume flow of a person to be measured;

connecting a pressure sensor via a first gas line to the mouthpiece upstream of the flow diaphragm;

connecting a breath alcohol sensor, via an inlet channel, to the mouthpiece downstream of the flow diaphragm and, via a second gas line, to a sampling system for taking a respiratory gas sample from the respiratory gas volume flow;

receiving measured signals of the pressure sensor and the breath alcohol sensor at an evaluation and control unit;

using the evaluation and control unit to actuate the sampling system;

determining a discharged respiratory gas volume by the evaluation and control unit based on the pressure of the respiratory gas volume flow measured at the diaphragm and by time integration;

actuating the sampling system by the evaluation and control unit for a respiratory gas sampling in the breath alcohol sensor at two different time points after the beginning of the respiratory gas volume flow detected by means of the pressure sensor with the volume of the first respiratory gas sample at most 40% of the volume of the second respiratory gas sample and the second respiratory gas sample is taken only if a certain, predetermined respiratory gas volume is reached within a certain, predetermined time.

4. A process in accordance with claim 3, wherein the second respiratory gas sample is taken if the overall exhaled respiratory gas volume is at least 1 L and if at least 4 seconds have passed since the beginning of the detection of the respiratory gas volume flow exhaled by a person.

5. A device for measuring breath alcohol, the device comprising:
- a mouthpiece defining a flow passage for receiving the exhaled respiratory gas volume flow of a person to be measured, the flow passage having a flow restriction providing a pressure drop in the flow passage;
- a pressure sensor connected to the mouthpiece upstream of said flow restriction;
- a breath alcohol sensor;
- a channel connected to said mouthpiece downstream of said flow restriction;
- sampling means for providing respiratory gas samples of the respiratory gas volume flow from said channel to said breath alcohol sensor in a time sequence with a sample volume of a first respiratory gas sample being at most 40% of a volume of a second respiratory gas sample;
- an evaluation and control unit receiving measured signals of said pressure sensor and actuating said sampling system.

6. A device in accordance with claim 1, wherein said sampling means comprises two magnets acting on a displacement member with a first magnet providing a displacement member stroke that is 30% to 40% of a displacement member stroke produced by said second magnet.

* * * * *